(12) United States Patent
Berghof et al.

(10) Patent No.: US 6,706,472 B2
(45) Date of Patent: Mar. 16, 2004

(54) GROUP OF NUCLEIC ACID MOLECULES SALMONELLA DETECTION, NUCLEIC ACIDS, KIT AND USE

(75) Inventors: Cornelia Berghof, Berlin (DE); Alexander Gasch, Berlin (DE); Pia Scheu, Berlin (DE); Freimut Wilborn, Berlin (DE)

(73) Assignee: Biotecon Diagnostics GmbH, Berlin (DE)

( * ) Notice: Subject to any disclaimer, the term of this patent is extended or adjusted under 35 U.S.C. 154(b) by 0 days.

(21) Appl. No.: 09/485,434

(22) PCT Filed: Aug. 12, 1998

(86) PCT No.: PCT/EP98/05129

§ 371 (c)(1),
(2), (4) Date: Apr. 14, 2000

(87) PCT Pub. No.: WO99/07886

PCT Pub. Date: Feb. 18, 1999

(65) Prior Publication Data

US 2003/0096228 A1 May 22, 2003

(30) Foreign Application Priority Data

Aug. 12, 1997 (DE) .......................................... 197 34 940

(51) Int. Cl.[7] .......................... C12Q 1/68; C12P 19/34; C07H 21/04

(52) U.S. Cl. .......................... 435/6; 435/91.1; 435/91.2; 536/23.1; 536/24.3; 536/24.32

(58) Field of Search .......................... 435/6, 91.1, 91.2; 536/23.1, 24.3, 24.32

(56) References Cited

U.S. PATENT DOCUMENTS

| | | | | | |
|---|---|---|---|---|---|
| 5,622,854 | A | * | 4/1997 | Draper | 435/366 |
| 5,714,321 | A | * | 2/1998 | Hogan et al. | 435/6 |
| 5,744,368 | A | * | 4/1998 | Goldgaber et al. | 436/501 |
| 6,004,747 | A | * | 12/1999 | Olsen et al. | 435/6 |

FOREIGN PATENT DOCUMENTS

| EP | WO 95/33851 | * | 12/1995 | 435/6 |
|---|---|---|---|---|

OTHER PUBLICATIONS

McClelland et al., Nature, 2001, vol. 413, pp. 852–856.*

* cited by examiner

*Primary Examiner*—Jehanne Souaya
(74) *Attorney, Agent, or Firm*—Frommer Lawrence & Haug LLP; Ronald R. Santucci

(57) ABSTRACT

The present invention relates to a nucleic acid molecule or molecules and to a process for the detection of bacteria of the Salmonella genus. The invention relates also to a test kit or test kits for carrying out the mentioned detection processes.

9 Claims, No Drawings

SEQUENCE LISTING

<160> NUMBER OF SEQ ID NOS: 13

<210> SEQ ID NO 1
<211> LENGTH: 20
<212> TYPE: DNA
<213> ORGANISM: Salmonella enterica

<400> SEQUENCE: 1
atggatcaga atacgccccg                 20

<210> SEQ ID NO 2
<211> LENGTH: 20
<212> TYPE: DNA
<213> ORGANISM: Salmonella enterica

<400> SEQUENCE: 2
atggatcaga atacaccccg                 20

<210> SEQ ID NO 3
<211> LENGTH: 20
<212> TYPE: DNA
<213> ORGANISM: Salmonella enterica

<400> SEQUENCE: 3
cagaatacgc cccgttcggc                                          20

<210> SEQ ID NO 4
<211> LENGTH: 20
<212> TYPE: DNA
<213> ORGANISM: Salmonella enterica

<400> SEQUENCE: 4
cagaatacac cccgttcggc                                          20

<210> SEQ ID NO 5
<211> LENGTH: 20
<212> TYPE: DNA
<213> ORGANISM: Salmonella enterica

<400> SEQUENCE: 5
cagaatacgc cccgttcagc                                          20

<210> SEQ ID NO 6
<211> LENGTH: 20
<212> TYPE: DNA
<213> ORGANISM: Salmonella enterica

<400> SEQUENCE: 6
caacctaact tctgcgccag                                          20

<210> SEQ ID NO 7
<211> LENGTH: 20
<212> TYPE: DNA
<213> ORGANISM: Salmonella enterica

<400> SEQUENCE: 7
caacctaact tctgcaccag                                          20

<210> SEQ ID NO 8
<211> LENGTH: 20
<212> TYPE: DNA
<213> ORGANISM: Salmonella enterica

<400> SEQUENCE: 8
caacctaacc tctgcgccag                                          20

<210> SEQ ID NO 9
<211> LENGTH: 20
<212> TYPE: DNA
<213> ORGANISM: Salmonella enterica

<400> SEQUENCE: 9
caacctaact tctgcgccag                                          20

<210> SEQ ID NO 10
<211> LENGTH: 20
<212> TYPE: DNA
<213> ORGANISM: Salmonella enterica

<400> SEQUENCE: 10
cagcctaact tctgcgccag                                          20

```
<210> SEQ ID NO 11
<211> LENGTH: 25
<212> TYPE: DNA
<213> ORGANISM: Salmonella enterica

<400> SEQUENCE: 11
agccaaccat tgctaaattg gcgca                                  25

<210> SEQ ID NO 12
<211> LENGTH: 24
<212> TYPE: DNA
<213> ORGANISM: Salmonella enterica

<400> SEQUENCE: 12
ggtagaaatt cccagcgggt actg                                   24

<210> SEQ ID NO 13
<211> LENGTH: 24
<212> TYPE: DNA
<213> ORGANISM: Salmonella enterica

<400> SEQUENCE: 13
tttgcgacta tcaggttacc gtgg                                   24
```

GROUP OF NUCLEIC ACID MOLECULES SALMONELLA DETECTION, NUCLEIC ACIDS, KIT AND USE

In the foodstuffs and pharmaceutical industries the contamination of products by pathogenic microorganisms by way of the raw materials used or during the production or packaging processes poses a major problem. Salmonellae are among the most serious pathogens transmitted to humans through foodstuffs. Since the detection and identification of Salmonellae by conventional microbiological detection processes is very time-consuming—at least five days are required for the increase in quantity and subsequent serotyping required by legal regulations (LMBG, FDA)—there is a great need for alternative rapid methods.

In recent years, a number of new methods have been developed for routine use to detect microorganisms. These include immunological processes based on the use of polyvalent or monoclonal antibodies and processes in which nucleic acid probes are used for detection by means of hybridisation to organism-specific nucleic acids. Further methods that have been described are those processes based on a specific nucleic acid amplification, with or without a subsequent confirmation reaction by nucleic acid hybridisation. Suitable processes for the amplification of nucleic acids are, for example, polymerase chain reaction [PCR] [U.S. Pat. Nos. 4,683,195; 4,683,202; and 4,965,188], ligase chain reaction [WO Publication 89/09835], "self-sustained sequence replication" [EP 329 822], the "transcription based amplification system" [EP 310 229] and the Qβ RNA-replicase system [U.S. Pat. No. 4,957,858].

The mentioned nucleic-acid-based processes are so sensitive that, unlike conventional microbiological processes, a lengthy increase in quantity of the microorganism to be detected from the sample to be investigated is unnecessary. An investigation of the presence or absence of, for example, Salmonellae is therefore generally concluded within one working day when using the mentioned nucleic-acid-based processes.

Some nucleic acid sequences for detecting Salmonellae by polymerase chain reaction are known. A disadvantage is, however, that when using those nucleic acid sequences as primers in the polymerase chain reaction false positive results [WO 95/33854] or false negative results [WO 92/01056; WO 95/00664; WO 92/01056; WO 93/04202] occur. In other cases, only an insufficient number of strains of all 7 Salmonellae subspecies have been studied [WO 92/08805; WO 94/25597; DE 4337295], so that thus far it is unclear whether the nucleic acid sequences in question are suitable for detecting all Salmonella strains.

An advantage of, for example, the primers and probes described in International Patent Application WO 95/00664 is that they allow the highly selective detection of bacteria of the Salmonella genus without the occurrence of false positive results. A disadvantage when using the oligonucleotides according to WO 95/00664 in amplification processes such as polymerase chain reaction is, however, the fact that none of the described primer pairs enable detection of all the representatives of the 7 Salmonella subspecies. For example, when using the primers ST11/ST15, a number of representatives of subspecies IIIa (subsp. *arizonae*) are not detected, and when using the primers ST11/ST14 a number of representatives of subspecies I (subsp. *enterica* Serovar. Blockley) and of subspecies IIIa (subsp. *arizonae*) are not detected.

An aim of the invention described herein was to optimise the detection processes described in WO 95/00664 by finding nucleic acid sequences the use of which as primers and/or probes ensures as complete detection as possible of all the representatives of the Salmonella genus.

According to an embodiment, the problem underlying the invention is solved by a set of nucleic acid molecules by means of which, in a process for the detection of representatives of *Salmonella enterica* subsp. *enterica, salamae, arizonae, diarizonae, houtenae, bongori* and *indica*, all the representatives of those subspecies can be detected, the set being obtainable by (a) obtaining or deriving a first nucleic acid molecule (nucleic acid molecule 1) in a manner known per se using a nucleic acid isolate of a representative of one of the mentioned *Salmonella enterica* subspecies, which first nucleic acid molecule is specifically suitable as primer or probe for the detection of that representative or of further or all representatives of that one *Salmonella enterica* subspecies and possibly also of representatives of further *Salmonella enterica* subspecies, (b) obtaining or deriving a second nucleic acid molecule (nucleic acid molecule 2) in a manner known per se using a nucleic acid isolate of a different representative of one of the mentioned *Salmonella enterica* subspecies, which second nucleic acid molecule is specifically suitable as primer or probe for the detection of that representative or of further or all representatives of that different *Salmonella enterica* subspecies and possibly also of representatives of others of the mentioned Salmonella enterica subspecies, and (c) unless it is already possible to detect all the representatives of the mentioned *Salmonella enterica* subspecies using the nucleic acid molecules obtainable according to (a) and (b), continuing to obtain or derive nucleic acid molecules according to (a) and/or (b) until all the representatives of the mentioned *Salmonella enterica* subspecies can be detected using the obtained or derived set of nucleic acid molecules.

A derived nucleic acid molecule may be a nucleic acid molecule that can be hybridised with the obtained nucleic acid molecule and that preferably has the same number of bases, possible hybridisation conditions being:

temperature $\geq 25°$ C. and 1M NaCl concentration.

A derived nucleic acid molecule may be, for example, a nucleic acid molecule the sequence of which has been determined by computer design and that has subsequently been manufactured and obtained by chemical synthesis.

The solution to the problem underlying the invention can also be described as the provision of one or more nucleic acid molecule(s) Y (Z, . . . ), that(those) nucleic acid molecule(s) being characterised in that the use of that(those) nucleic acid molecule(s)—in addition to the use of a nucleic acid molecule (X)—in a process for the detection of bacteria of the Salmonella genus enables the detection also of Salmonella strains or Salmonella isolates that cannot be detected or can be detected only with relatively low sensitivity using the nucleic acid molecule (X).

The set of nucleic acid molecules according to the invention can be characterised in that the nucleic acid isolates comprise or are phylogenetically conserved base sequences or regions of those base sequences. For the term "phylogenetically conserved base sequence", see, for example, WO 95/00664 or Herder's Lexikon der Biochemie und Molekularbiologie, supplemented 1995, page 132, spectrum, production, etc.

The set of nucleic acid molecules according to the invention can be characterised in that the individual nucleic acid molecules or some of the nucleic acid molecules hybridise to (i) different phylogenetically conserved base sequences, or
(ii) one and the same phylogenetically conserved base sequence at non-overlapping sequence regions, or
(iii) one and the same phylogenetically conserved base sequence at overlapping sequence regions.

The set of nucleic acid molecules according to the invention or a set of nucleic acid molecules according to the invention by means of which, in a process for the detection of representatives of *Salmonella* enterica subsp. *enterica, salamae, arizonae, diarizonae, houtenae, bongori* and *indica*, all the representatives of those subspecies can be detected, can be characterised in that the set for an individual nucleic acid molecule, for a number of its individual nucleic acid molecules or for each of its individual nucleic acid molecules in each case comprises at least one further nucleic acid molecule that, in a region of at least 10 successive nucleotides of their nucleotide chain, corresponds to less than 100% but to at least 80% of the base sequence.

Such a set of nucleic acid molecules according to the invention can be characterised in that the set for an individual nucleic acid molecule, for a number of its individual nucleic acid molecules or for each of its individual nucleic acid molecules in each case comprises at least one further nucleic acid molecule that, in a region of at least 10 successive nucleotides of their nucleotide chain, differs from the other or further nucleic acid molecule in precisely one base position.

A set of nucleic acid molecules according to the invention can be characterised in that it comprises one or more, but not exclusively, nucleic acid molecules that are fragments of the SEQ ID NO 1 according to WO 95/00664 or of its complementary sequence.

A set of nucleic acid molecules according to the invention can also be characterised in that the individual nucleic acid molecules hybridise to the same strand of nucleic acid isolates of representatives of *Salmonella enterica* subspecies that are being subjected to the process for their detection.

The problem underlying the invention is also solved by a nucleic acid molecule that belongs to a set of nucleic acid molecules according to the invention or that can be used for such a set, the nucleic acid molecule being characterised in that, in a region of at least 10 successive nucleotides of its nucleotide chain, the sequence of the nucleic acid molecule corresponds exactly to a sequence region of at least one representative of the mentioned *Salmonella enterica* subspecies, the sequence region comprising or being a phylogenetically conserved base sequence or a region of that base sequence.

Such a nucleic acid molecule according to the invention can be characterised in that, in a region of at least 10 successive nucleotides of its nucleotide chain, it is 100% or at least 80% identical to a corresponding number of successive nucleotides of one or more of the following sequences or their complementary sequences:

| | |
|---|---|
| ATGGATCAGAATACGCCCCG | SEQ ID NO:1 |
| ATGGATCAGAATACACCCCG | SEQ ID NO:2 |
| CAGAATACGCCCCGTTCGGC | SEQ ID NO:3 |
| CAGAATACACCCCGTTCGGC | SEQ ID NO:4 |
| CAGAATACGCCCCGTTCAGC | SEQ ID NO:5 |

-continued

| | |
|---|---|
| CAACCTAACTTCTGCGCCAG | SEQ ID NO:6 |
| CAACCTAACTTCTGCACCAG | SEQ ID NO:7 |
| CAACCTAACCTCTGCGCCAG | SEQ ID NO:8 |
| CAACCTAACTTCTGCGCCAG | SEQ ID NO:9 |

The problem underlying the invention is also solved by a nucleic acid molecule characterised in that, in respect of its sequence, it is homologous to an above-characterised nucleic acid molecule according to the invention and, in at least 10 successive nucleotides of its nucleotide chain,
(i) is identical to an above-characterised nucleic acid molecule according to the invention, or
(ii) differs from an above-characterised nucleic acid molecule according to the invention in not more than one nucleotide, or
(iii) differs from an above-characterised nucleic acid molecule according to the invention in not more than two nucleotides.

A nucleic acid molecule according to the invention can be characterised in that it is from 10 to 250 nucleotides long and preferably from 15 to 30 nucleotides long.

A nucleic acid molecule according to the invention can also be characterised in that it is single-stranded or has a complementary strand.

A nucleic acid molecule according to the invention can also be characterised in that it is present
(i) as DNA, or
(ii) as RNA corresponding to (i), or
(iii) as PNA, the nucleic acid molecule where appropriate having been modified or labelled in a manner known per se for analytical detection processes, especially detection processes based on hybridisation and/or amplification.

A nucleic acid molecule according to the invention can also be characterised in that it is a modified or labelled nucleic acid molecule in which up to 20% of the nucleotides of at least 10 successive nucleotides of its nucleotide chain are building blocks known per se as probes and/or primers, especially nucleotides that do not occur naturally in bacteria.

A nucleic acid molecule according to the invention can also be characterised in that it is a modified or labelled or additionally modified or labelled nucleic acid molecule that comprises, in a manner known per se for analytical detection processes, one or more radioactive groups, coloured groups, fluorescent groups, groups for immobilisation on a solid phase, groups for an indirect or direct reaction, especially for an enzymatic reaction, preferably using antibodies, antigens, enzymes and/or substances having an affinity for enzymes or enzyme complexes, and/or other modifying or modified groups of nucleic-acid-like structure that are known per se.

The problem underlying the invention is also solved by a kit for analytical detection processes, especially for the detection of bacteria of the Salmonella genus, that kit being characterised by
(i) a set of nucleic acid molecules according to the invention, or
(ii) one or more nucleic acid molecules according to the invention.

A kit according to the invention can thus comprise a set of nucleic acid molecules according to the invention or one or more nucleic acid molecules according to the invention, there additionally being provided the other customary components for nucleic acid hybridisations or nucleic acid amplifications, for example a polymerase, a reverse transcriptase, a ligase or an RNA-polymerase, see, for example, WO 95/00664.

A set of nucleic acid molecules of the kit according to the invention will preferably be produced synthetically in at least two separate synthesis batches. The kit according to the invention preferably does not comprise any degenerate nucleic acid molecules.

Finally, the problem underlying the invention is solved by the use of a set of nucleic acid molecules according to the invention or of a kit according to the invention to detect the presence or absence of bacteria belonging to a group of bacteria of the Salmonella genus, especially of representatives of the above-mentioned *Salmonella enterica* subspecies.

For the use according to the invention, nucleic acid hybridisation and/or nucleic acid amplification can be carried out.

As nucleic acid amplification, there can be carried out a polymerase chain reaction (PCR).

For the use according to the invention, differences between the genomic DNA and/or RNA of the bacteria to be detected and of the bacteria that are not to be detected can be determined at at least one nucleotide position in the region of a nucleic acid molecule according to the invention and representatives of a group of bacteria of the Salmonella genus can be detected, especially representatives of the mentioned *Salmonella enterica* subspecies.

To detect Salmonellae by means of nucleic acid hybridisation or amplification, Salmonella-specific oligonucleotides are used. Salmonella-specific oligonucleotides are nucleic acid molecules, from 10 to 250 bases (preferably from 15 to 30 bases) long, the base sequence of which is characteristic for Salmonellae: when using such oligonucleotides as primers or probes—with suitable reaction conditions—hybridisation/amplification takes place only when DNA of the Salmonellae to be detected is present in the test sample, but not when DNA of other bacteria is present.

As described below, given certain prerequisites non-specific oligonucleotides may also be used as primers or probes. Such oligonucleotides enable hybridisation and/or amplification not only when Salmonella-DNA is present in the sample but also in the presence of DNA of a bacterium or of a number of bacteria not belonging to the Salmonella genus.

Since, in highly conserved gene regions, substitutions (e.g. point mutations) in the DNA can occur even in the case of very closely related bacteria, comprehensive DNA sequencing or specificity tests (e.g. by carrying out PCR) are necessary to select suitable oligonucleotides. This applies equally to bacteria to be detected (i.e. Salmonellae) and to bacteria that are not to be detected (i.e. bacteria not belonging to the Salmonella genus).

To detect Salmonellae, firstly nucleic acids, preferably genomic DNA, are released from the cells contained in a sample or bacterial culture to be investigated. By means of nucleic acid hybridisation, the direct detection of Salmonella nucleic acids in the sample to be investigated can then be effected using the Salmonella-specific oligonucleotides according to the invention as probe. Various processes known to the person skilled in the art are suitable for that purpose, such as, for example, "Southern blot" or "dot blot".

Preference is given, however, above all on account of the relatively high sensitivity, to indirect detection in which the DNA/RNA sequences sought are firstly amplified by means of the above-mentioned processes for amplifying nucleic acids, preferably PCR. The amplification of DNA/RNA is effected by using Salmonella-specific oligonucleotides. In that process specific amplification products are formed only when Salmonella-DNA/RNA is present in the sample to be investigated. The specificity of the detection process can be increased by a subsequent detection reaction using Salmonella-specific oligonucleotides as probes. It is also possible to use non-specific oligonucleotides as probes.

Alternatively, amplification can also be carried out in the presence of one or more non-specific oligonucleotides, so that possibly also DNA/RNA of other microorganisms that are not to be detected may be amplified. Such an amplification process is generally less specific and should therefore be backed up by a subsequent detection reaction using Salmonella-specific oligonucleotides as probe.

Various processes by which amplification products formed in the indirect processes can be detected are known to the person skilled in the art. These include, inter alia, visualisation by means of gel electrophoresis, the hybridisation of probes on immobilised reaction products [coupled to nylon or nitrocellulose filters ("Southern blots") or, for example, on beads or microtitre plates] and the hybridisation of the reaction products on immobilised probes (e.g. "reverse dot blots" or beads or microtitre plates coupled with probes).

A large number of different variants have been described by means of which the described Salmonella-specific or non-specific oligonucleotides for use as probes and/or primers in direct or indirect detection processes can be labelled or modified. They may comprise, for example, radioactive, coloured or fluorescent groups or groups that enable immobilisation on a solid phase or groups that have been modified or that modify in some other way, such as, for example, antibodies, antigens, enzymes or other substances having an affinity for enzymes or enzyme complexes. Probes and primers may be either naturally occurring or synthetically produced double- or single-stranded DNA or RNA or modified forms of DNA or RNA, such as, for example, PNA (in those molecules the sugar units have been replaced by amino acids or peptides). Individual nucleotides or a number of nucleotides of the probes or primers may be replaced by analogous building blocks (such as, for example, nucleotides that do not naturally occur in the target nucleic acid). In the case of the above-mentioned indirect detection processes, the detection can be carried out also by means of an internally labelled amplification product. That can be effected, for example, by the integration of modified nucleoside triphosphates (e.g. coupled with digoxygenin or fluorescein) during the amplification reaction.

Suitable Salmonella-specific oligonucleotides according to the invention are nucleic acids, preferably from 15 to 30 bases long, that correspond, at least in a 10 base long sequence, to sequences 1 to 10 or to their complementary sequences. Relatively small differences (1 or 2 bases) in that 10 base long sequence are possible without loss of the requisite specificity in the amplification and/or hybridisation. The person skilled in the art will know that in the case of such relatively small differences the reaction conditions need to be altered accordingly.

In order to enable complete detection of all the Salmonella strains using the DNA region outlined in WO 95/00664, comprehensive DNA sequence analyses were necessary. The sequence of that DNA region was determined from 37 selected Salmonella strains of all 7 subspecies (for most of the strains, the sequence of the DNA region between primers ST15 and ST11; this corresponds to position 1275 to 1654 of SEQ ID NO: 1 in WO 95/00664). Possible experimental procedures will be known to the person skilled in the art and will not be described here in detail; a brief summary of the results will be given. DNA of the selected Salmonella strains was prepared by standard procedures and the relevant region was amplified by PCR and subsequently sequenced. In the PCR and the subsequent sequencing, the following primers were used for most of the Salmonella strains:

ST11: AGCCAACATTGCTAAATTGGCGCA (SEQ ID NO:11) (see claim 3, WO 95/00664)

ST15: GGTAGAAATTCCCAGCGGGTACTG (SEQ ID NO:12) (see claim 3, WO 95/00664)

Since, however, no amplification, or only insufficient amplification, occurred with that primer pair with a number of strains of subspecies IIIa, IV, V and VI, in those cases the following primers were used for the PCR and sequencing:

ST11:AGCCAACCATTGCTAAATTGGCGCA (see claim 3, WO 95/00664)

ST14:TTTGCGACTATCAGGTTACCGTGG (SEQ ID NO:13) (see claim 3, WO 95/00664).

A comparison of the DNA sequences of all 37 Salmonella strains showed that while it was as a whole a conserved DNA region, the degree of conservation appeared at first glance to have only limited suitability for deriving Salmonella-specific oligonucleotides. Even in the most highly conserved regions, base substitutions were observed in some of the sequenced strains. Interestingly, it was found that many of the base substitutions occur only within a subgroup and that the substitutions are moreover generally conserved within that subgroup. This suggested the possibility of using more than two primers in the PCR in order to enable amplification also of those variants in which one or more base substitutions are present in the region of the primer binding sites. As the person skilled in the art will know, for that purpose there are customarily used degenerate primers or primers having deoxyinosin at the variable sites. A number of degenerate oligonucleotides that were potentially suitable as primers for the detection of all *Salmonella enterica* subspecies were therefore deduced from the above-mentioned sequence comparison. It was found, however, that those degenerate primers have only limited suitability for PCR detection since they result in an increase in the occurrence of non-specific reaction products, especially in the case of sequence regions of high complexity. Since the sensitivity of the PCR detection generally suffers from the occurrence of such non-specific reaction products, a different procedure was tried. "Complementing" primers were used in the PCR. In contrast to degenerate primers, in which all the possible combinations of the individual base substitutions are represented in the primer mixture (number of primers=$2^x \times 3^y \times 4^z$ where x, y and z are the number of positions at which two, three or four different bases are observed in the region of the primer binding site), in such complementing primers only the actually occurring sequences are present. The advantage over degenerate primers lies in the lesser complexity of the primer mixture according to the invention, as a result of which the probability that non-specific amplification products will be formed is markedly reduced. As has been shown in a number of experiments, this is especially advantageous in PCR detection using samples having a high content of "non-specific" DNA (DNA that does not come from bacteria to be detected) since, otherwise, the sensitivity of the detection may be radically reduced.

A major advantage when using complementing oligonucleotides/primers lies in the possibility of optimising existing detection processes. For example, it is possible that individual false negative results can be eliminated by additionally using in the PCR and/or hybridisation reaction oligonucleotides comprising the sequence of the previously undetected strains.

The DNA sequence comparison yielded a number of relatively short DNA regions that appeared to be potentially suitable for the strategy described (use of in total ≧3 primers in the PCR) for optimising the Salmonella detection process. The following Example is given by way of clarification.

EXAMPLE 1

Detection of Salmonella Strains of all 7 Subspecies by Polymerase Chain Reaction The following 3 sections of the sequenced DNA region are to serve as examples for the sequence variations observed:

Section I (position 1336 to 1355 of SEQ ID NO: 1 in WO 95/00664)

| ATGGATCAGAATACGCCCCG | SEQ ID NO:1 |
| ATGGATCAGAATACACCCCG | SEQ ID NO:2 |

Section II (position 1342 to 1361 of SEQ ID NO: 1 in WO 95/00664)

| CAGAATACGCCCCGTTCGGC | SEQ ID NO:3 |
| CAGAATACACCCCGTTCGGC | SEQ ID NO:4 |
| CAGAATACGCCCCGTTCAGC | SEQ ID NO:5 |

Section III (complementary to position 1483 to 1502 of SEQ ID NO: 1 in WO 95/00664)

| CAACCTAACTTCTGCGCCAG | SEQ ID NO:6 |
| CAACCTAACTTCTGCACCAG | SEQ ID NO:7 |
| CAACCTAACCTCTGCGCCAG | SEQ ID NO:8 |
| CAACCTAACTTCTGCGGCAG | SEQ ID NO:9 |
| CAACCTAACTTCTGCGGCAG | SEQ ID NO:10 |

To test whether those sequence sections are suitable for detecting all the Salmonella strains of the 7 subspecies, the oligonucleotides Sa 1 to 10 were used in the PCR in the following combinations:

| Primer combination 1 | |
|---|---|
| Sa1/Sa2 | (each in a final concentration of 0.2 μM) |
| Sa6/Sa7/Sa8/Sa9/Sa10 | (each in a final concentration of 0.08 μM) |
| Primer combination 2 | |
| Sa3/Sa4/Sa5 | (each in a final concentration of 0.13 μM) |
| Sa6/Sa7/Sa8/Sa9/Sa10 | (each in a final concentration of 0.08 μM) |

DNA was isolated by standard processes from pure cultures of the Salmonella strains listed in Table 1a. Approximately from 10 to 100 ng of each of those DNA preparations was then used in the PCR in the presence of primer combination 1 or primer combination 2, 200 μM of dNTP's (Boehringer Mannheim), 1.5 mM $MgCl_2$, 16 mM $(NH_4)_2SO_4$, 67 mM Tris/HCl (pH 8.8), 0.01% Tween 20 and 0.03 U/μl Taq-polymerase (Biomaster). The PCR was carried out in a Perkin-Elmer 9600 thermocycler having the following thermoprofile:

| initial denaturing | 95° C. | 5 min |
|---|---|---|
| amplification (35 cycles) | 95° C. | 30 sec |
| | 63° C. | 90 sec |
| final synthesis | 72° C. | 5 min |

After the end of the PCR reaction, the amplification products were separated by means of agarose gel electrophoresis and visualised by staining with ethidium bromide. The expected product of 167 bp length (primer combination 1) or of 161 bp length (primer combination 2 was observed in all cases in which DNA of strains of the Salmonella genus was present (compare Table 1a), but not in the presence of DNA of other tested bacteria (compare Table 1b). After the end of the run, the DNA contained in the gels was transferred by standard methods to nylon filters and hybridised with the oligonucleotide ST14 (TTTGCGACTATCAGGTTA CCGTGG (SEQ ID NO:13) (see claim 3, WO 95/00664)) labelled at the 5' end with digoxygenin to test the base specificity especially sensitively. Hybridisation was effected in 5×SSC, 2% blocking reagent, 0.1% lauryl sarcosine, 0.02% SDS and 5 pmol/ml of probe for 4 hours at 60° C. Washing was carried out in 2×SSC, 0.1% SDS for 2×15 minutes at 60° C. Detection was carried out according to standard methods using anti-digoxygenin/alkaline phosphate conjugates in the presence of 5-bromo-4-chloro-3-indolyl phosphate and 4-nitro-blue tetrazolium chloride (Boehringer Mannheim).

A band was observed on the filters only in those cases in which a band had previously been visible on the agarose gel (see Table 1a). Thus, the presence of the 296 tested Salmonella strains from each of the 7 subspecies was detected both by PCR and by hybridisation. A positive signal was obtained for each of those strains with primer combination 1, primer combination 2 and, in the subsequent confirmation reaction, by hybridisation with the probe ST14. By contrast, none of the tested bacterial strains not belonging to that genus was detected using this system.

TABLE 1a

Positive Salmonella strains in PCR amplification using the two primer combinations 1 or 2 and in the subsequent hybridisation using the oligonucleotide ST14.

| No. | Subspecies | Serogroup | Serovar. |
|---|---|---|---|
| | S. enterica subsp. Enterica | B | Abony |
| | | | Abortusovis |
| | | | Africana |
| | | | Agona |
| | | | Agona, lactose + |
| | | | Arechavaleta |
| | | | Brandenburg |
| | | | Bredeney |
| | | | Chester |
| | | | Coeln |
| | | | Derby O: 5 − |
| | | | Duisburg |
| | | | Duisburg, monophase |
| | | | Heidelberg |
| | | | Heidelberg, O5 − |
| | | | I 4, 12: d: − |
| | | | I 4, 12: −: − |

TABLE 1a-continued

Positive Salmonella strains in PCR amplification using the two primer combinations 1 or 2 and in the subsequent hybridisation using the oligonucleotide ST14.

| No. | Subspecies | Serogroup | Serovar. |
|---|---|---|---|
| | | | I 9, 12: 1, v: − |
| | | | Indiana |
| | | | Kiambu |
| | | | Kunduchi |
| | | | Paratyphi B |
| | | | Paratyphi B H 1, 2 negative |
| | | | Paratyphi B O5 − |
| | | | Reading |
| | | | Saintpaul O5 − |
| | | | Saintpaul |
| | | | Sandiego |
| | | | Schleisheim |
| | | | Schwarzengrund |
| | | | Stanley |
| | | | Stanleyville |
| | | | Typhimurium |
| | | | Typhimurium 4: i: 1, 2 (O: 5−) |
| | | | Typhimurium O: 5 − |
| | | | Typhimurium, TA 1535 |
| | | | Typhimurium, TA 1537 |
| | | | Typhimurium, TA 1538 |
| | | | Typhimurium, TA 97 |
| | | | Typhimurium, TA 98 |
| | | | Typhimurium, TA 100 |
| | | $C_1$ | Augustenborg |
| | | | Bareilly |
| | | | Braenderup |
| | | | Choleraesuis |
| | | | Choleraesuis var. Decatur |
| | | | Choleraesuis var. Kunzendorf |
| | | | Colindale |
| | | | Concord |
| | | | Infantis |
| | | | Isangi |
| | | | Lille |
| | | | Livingstone |
| | | | Mbandaka |
| | | | Mikawasima |
| | | | Montevideo |
| | | | Ohio |
| | | | Oranienburg |
| | | | Oslo |
| | | | Richmond (2 isolates tested) |
| | | | Rissen |
| | | | Singapore |
| | | | Tennessee |
| | | | Thompson (2 isolates tested) |
| | | | Virchow |
| | | | I 6, 7: −: − (2 isolates tested) |
| | | $C_2 C_3$ | Albany (2 isolates tested) |
| | | | Altona |
| | | | Apeyeme |
| | | | Bardo |
| | | | Blockley |
| | | | Bovismorbificans |
| | | | Charlottenburg |
| | | | Cottbus |
| | | | Emek |
| | | | Ferruch |
| | | | Glostrup |
| | | | Goldcoast |
| | | | Haardt |
| | | | Hadar |
| | | | Kentucky |
| | | | Litchfield |
| | | | Manchester |
| | | | Manhattan |
| | | | Molade |
| | | | Munchen |
| | | | Newport |
| | | | Takoradi |
| | | | I 6, 8: −: − |
| | | | I 8, 20: −: − |

TABLE 1a-continued

Positive Salmonella strains in PCR amplification using the two primer combinations 1 or 2 and in the subsequent hybridisation using the oligonucleotide ST14.

| No. | Subspecies | Serogroup | Serovar. |
|---|---|---|---|
| | | $D_1$ | Dublin |
| | | | Durban |
| | | | Enteritidis |
| | | | Enteritidis plasmid phage 37MD |
| | | | EnteritidiS PT 4/6 |
| | | | Enteritidis, phage |
| | | | Gallinarum |
| | | | Gallinarum-Pullorum |
| | | | Israel |
| | | | Javiana |
| | | | Kapemba |
| | | | Napoli |
| | | | Panama |
| | | | Pullorum |
| | | | I 9, 12: –: – |
| | | $D_2$ | Plymoth |
| | | $E_1$ | Amager |
| | | | Amsterdam O: –, 15+, 34+ |
| | | | Anatum |
| | | | Anatum O 15+ |
| | | | Anatum O: 10–, O: 15+ |
| | | | Birmingham |
| | | | Butantan |
| | | | Falkensee |
| | | | Give |
| | | | Lexington |
| | | | London |
| | | | Meleagridis |
| | | | Munster |
| | | | Munster, O: 10–, 15+ |
| | | | Orion |
| | | | Orion O: 10 –, 15+ 34+ |
| | | | Sinstorf |
| | | | Stockholm |
| | | | Uganda (2 isolates tested) |
| | | | Vejle (2 isolates tested) |
| | | | Weltevreden |
| | | | Westhampton |
| | | | Zanzibar |
| | | | I 3, 10: –: 6 (monophase) |
| | | | I 10: –: 1, 6 |
| | | $E_4$ | Abaetuba |
| | | | Aberdeen |
| | | | Cannstatt |
| | | | Llandoff |
| | | | Senftenberg, delayed Lac. + |
| | | | I 1, 3, 19, : –: – |
| | | F | Chandans (2 isolates tested) |
| | | | Kisarawe |
| | | | Krefeld |
| | | | Liverpool |
| | | | Rubislaw |
| | | | Senftenberg |
| | | | Solt |
| | | | Telashomer |
| | | G | Grumpensis |
| | | | Havana |
| | | | Idikan |
| | | | Kedougou |
| | | | Poona |
| | | | Putten |
| | | | Worthington |
| | | | I 13, 23, : – |
| | | H | Caracas |
| | | | Charity |
| | | | Lindern |
| | | | Onderstepoort |
| | | | Sundsvall |
| | | | Gaminara |
| | | | Hvittingfoss |
| | | | Malstatt |
| | | | Saphra |
| | | J | Bonames |
| | | K | Cerro |
| | | L | Minnesota (2 isolates tested) |
| | | | Ruiru |
| | | M | Cotham |
| | | | Guildford |
| | | | Ilala |
| | | | Loeben |
| | | | Mundonobo |
| | | | Nima |
| | | | Patience |
| | | | Pomona |
| | | | Taunton |
| | | | Wedding |
| | | N | Aqua |
| | | | Morningside |
| | | | Urbana |
| | | O | Adelaide |
| | | | Alachua |
| | | | Ealing |
| | | | Haga |
| | | | Monschaui |
| | | P | Lansing |
| | | | Roan (2 isolates tested) |
| | | | Shettfield |
| | | Q | Kokomelemle |
| | | R | Johannesburg |
| | | S | Waycross (2 isolates tested) |
| | | T | Waral |
| | | U | Thetford |
| | | V | Koketime (2 isolates tested) |
| | | | Lawra |
| | | W | Suelldorf |
| | | X | I 47, $z_4$, $z_{23}$: (monophase) |
| | | | Mountpleasant |
| | S. enterica subsp. salamae | B | II 4, 12: a: – |
| | | $C_1$ | II 6, 7: d: 1, 7 |
| | | F | II 11: g, m, s, t: $z_{39}$ |
| | | I | II 16: g, m, s, t: – |
| | | J | II 17: c: $z_{39}$ |
| | | | II 17: b: e, n, x, $z_{15}$ |
| | | L | II 21: $z_{10}$: – |
| | | P | II 38: d: 1, 5 |
| | | R | II 1, 40: $z_{42}$: 1, 5, 7 |
| | | S | II 41: $z_{10}$, 1, 2 |
| | | T | II 42: r: – (3 isolates tested) |
| | | X | II 47: a: 1, 5 (2 isolates tested) |
| | | | II 47: b: 1, 5 (2 isolates tested) |
| | | | II 47: b: $z_6$ |
| | | Z | II 50: b: $z_6$ (5 isolates tested) |
| | | O: 58 | II 58: 1, $z_{13}$, $z_{28}$: $z_6$ |
| | S. enterica subsp. arizonae | J | IIIa 17: $z_4$, $z_{32}$: _ |
| | | K | IIIa 18: $z_4$, $z_{23}$: – |
| | | P | IIIa 38: 1, v: – |
| | | R | IIIa 40: $z_4$, $z_{24}$: – |
| | | S | IIIa 41: $z_4$, $z_{23}$: – |
| | | U | IIIa 43: g, $z_{51}$: – |
| | | V | IIIa 44: $z_4$, $z_{32}$: – |
| | | | IIIa 44: $z_{41}$, $z_{23}$: – |
| | | Y | IIIa 48: (1): – |
| | | | IIIa 48: g, $z_{51}$ : – |
| | | | IIIa 48: $z_{36}$: – |
| | | | IIIa 48: $z_4$, $z_{23}$: – |
| | | Z | IIIa 50: $z_4$, $z_{24}$: – |
| | | O: 51 | IIIa 51: $z_4$, $z_{23}$: – |
| | | | IIIa 51: g, $z_{51}$: – |
| | | O: 53 | IIIa 53: $z_4$, $z_{23}$, $z_2$: – |
| | | | IIIa 53: $z_{29}$: – |
| | | O: 62 | IIIa 62: $z_{36}$: – |
| | | O: 63 | IIIa 63: g, $z_{51}$: – |

TABLE 1a-continued

Positive Salmonella strains in PCR amplification
using the two primer combinations 1 or 2 and in the
subsequent hybridisation using the oligonucleotide ST14.

| No. | Subspecies | Serogroup | Serovar. |
|---|---|---|---|
|  | S. enterica subsp. diarizonae | $D_1$ | IIIb 1, 9, 12: y: $z_{39}$ |
|  |  | I | IIIb 16: k: – |
|  |  | J | IIIb 17: $z_{10}$, e, n, x, $z_{15}$ |
|  |  | O | IIIb 35: k: e, n, $z_{15}$ |
|  |  | P | IIIb 38: 1, v: $z_{53}$ |
|  |  |  | IIIb 38: 1, v: $z_{54}$ |
|  |  | T | IIIb 42: k: $z_{35}$ |
|  |  | X | IIIb 47: b: $z_6$ |
|  |  |  | IIIb 47: k: $z_{35}$ |
|  |  |  | IIIb 47: r: $z_{53}$ |
|  |  |  | IIIb 47: –: – |
|  |  | Y | IIIb 48: (k): $z_{53}$ |
|  |  | Z | IIIb 50: k: z |
|  |  |  | IIIb 50: r: z |
|  |  | O: 53 | IIIb 53: 1, k: z |
|  |  | O: 60 | IIIb 60: $z_{52}$: $z_{53}$ |
|  |  | O: 61 | IIIb 61: 1: z |
|  |  |  | IIIb 61: 1, v: 1, 5, 7 |
|  |  |  | IIIb 61: 1, v: 1, 5, 7: ($z_{57}$) |
|  |  |  | IIIb 61: r: $z_{53}$ |
|  | S. enterica subsp. houtenae | F | IV 11: $z_4$, $z_{23}$: – |
|  |  | I | IV 16: $z_4$, $z_{32}$: – |
|  |  | I | IV 16: $z_4$, $z_{32}$: – |
|  |  | J | IV 17: $z_{29}$: – |
|  |  | K | IV 18: $z_{36}$, $z_{38}$: – |
|  |  | L | IV 21: g, $z_{51}$: – |
|  |  | U | IV 43: $z_4$, $z_{23}$: – |
|  |  |  | IV 43: $z_4$, $z_{32}$: – |
|  |  | V | TV 44: $z_4$, $z_{32}$: – |
|  |  | Y | IV 48: $z_{29}$: – |
|  |  | Z | IV 50: $z_4$, $z_{23}$: – |
|  | S. enterica subsp. bongori | R | V 40: $z_{35}$: – |
|  |  |  | V 40: $z_{81}$: – |
|  |  | V | V 44: d: – |
|  |  |  | V 44 : $z_{39}$: – |
|  |  | Y | V 48 : $z_{35}$: – |
|  | S. enterica subsp. indica | S | VI 41: b: 1, 7 |
|  |  | W | VI 45: a: e, n, x, ($z_{17}$) |
|  |  | Y | VI 48: $z_{10}$: 1, 5 |
|  |  |  | VI 48: $z_{41}$: – |
|  |  |  | VI 1, v: $z_{67}$ |

Reference source: bgVV Berlin, (Robert von Ostertag Institut, Marienfelde) and Institut fur Mikrobiologie und Hygiene, Hamburg (Prof. Aleksic). The strains bearing the letters TA are strains used for the Ames Test (Maron, D. M. & Ames, B. N., Mutation Research 113, 173—215 (1983)).

TABLE 1b

Negative strains of non-Salmonella species in PCR
amplification using the two primer combinations 1 or 2 and
the subsequent hybridisation using the oligonucleotide ST 14

| No. | Species | Origin |
|---|---|---|
|  | Bacillus subtilis | ATCC 6051 |
|  | Citrobacter freundii | DSM 30040 |
|  | Clostridium bifermentans | DSM 630 |
|  | Enterobacter agglomerans | IfGB 0202 |
|  | Enterobacter cloacae | DSM 30054 |
|  | Erwinia carotovora | DSM 30168 |
|  | Escherichia coli | ATCC 8739 |
|  | Hafnia alvei | IfGB 0101 |
|  | Klebsiella oxytoca | DSM 5175 |
|  | Klebsiella pneumoniae | ATCC 13883 |
|  | Klebsiella oxytoca | DSM 5175 |
|  | Lactobacillus spec. | ATCC 20182 |
|  | Listeria monocytogenes | ATCC 19118 |
|  | Pediococcus domnatus | IfGB 0101 |
|  | Proteus vulgaris | DSM 2041 |
|  | Pseudomonsas fluorescens | DSM 6290 |
|  | Serratia marcescens | IfGB 0101 |
|  | Shigella flexneri | DSM 4782 |
|  | Staphylococcus aureus | ATCC 6538 |
|  | Yersinia enterocolitica | DSM 4780 |

What is claimed is:

1. A method of detecting the presence or absence of a subspecies of bacterium *Salmonella enterica*, comprising the steps of:
   (a) providing at least one isolated nucleic acid molecule selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10 and the complement of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10;
   (b) contacting the at least one isolated nucleic acid molecule of (a) with a test sample containing nucleic acids;
   (c) hybridizing and/or amplifying the nucleic acid molecules of the test sample with the at least one isolated nucleic acid molecule of (a); and
   (d) detecting nucleic acid hybrids formed between the nucleic acid molecules of the test sample and the at least one nucleic acid molecule of (a) and/or detecting amplified nucleic acid molecules of the test sample, thereby determining the presence or absence of a subspecies of the bacterium *Salmonella enterica* in the test sample.

2. The method of claim 1, wherein the amplifying of the nucleic acid molecules of the test sample is carried out by a polymerase chain reaction (PCR).

3. The method of claim 1, wherein the subspecies of *Salmonella enterica* is selected from the group consisting of *Salmonella enterica* subspecies *enterica, salamae, arizonae, diarizonae, houtenae, bongori* and *indica*.

4. A kit comprising: (i) one or more isolated nucleic acid molecules selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10 and the complement of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10, and (ii) optionally substances for analytical detection processes.

5. The kit of claim 4, wherein at least one isolated nucleic acid molecule is modified or labelled with a group selected from the group consisting of a radioactive group, a colored group, a fluorescent group, a group for immobilisation on a solid phase and a group allowing an indirect or direct enzyme reaction.

6. The kit of claim 5, wherein the group allowing an enzyme reaction is selected from the group consisting of antibodies, antigens, enzymes, substances having an affinity for enzymes and substances having an affinity for enzyme complexes.

7. The kit of claim 4, wherein the isolated nucleic acid molecule is single stranded.

8. The kit of claim 4, wherein the isolated nucleic acid molecule is double stranded.

9. The kit of claim 4, wherein the isolated nucleic acid molecules are produced synthetically and in at least two separate synthesis batches.

* * * * *